US012758194B2

(12) United States Patent
Waki et al.

(10) Patent No.: US 12,758,194 B2
(45) Date of Patent: Oct. 13, 2026

(54) ULTRASOUND VOLUME DATA FORMING APPARATUS AND ULTRASOUND VOLUME DATA FORMING PROGRAM

(71) Applicant: FUJIFILM Corporation, Tokyo (JP)

(72) Inventors: Koji Waki, Tokyo (JP); Yuko Sato, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 19/298,136

(22) Filed: Aug. 12, 2025

(65) Prior Publication Data

US 2026/0047823 A1 Feb. 19, 2026

(30) Foreign Application Priority Data

Aug. 15, 2024 (JP) ................................ 2024-135555

(51) Int. Cl.
*A61B 8/00* (2006.01)
*G06T 15/08* (2011.01)
*G06V 10/44* (2022.01)

(52) U.S. Cl.
CPC .......... *A61B 8/5215* (2013.01); *A61B 8/4245* (2013.01); *G06T 15/08* (2013.01); *G06V 10/44* (2022.01)

(58) Field of Classification Search
CPC ..... A61B 8/5215; A61B 8/4235; G06V 10/44
See application file for complete search history.

(56) References Cited

U.S. PATENT DOCUMENTS 5,899,861 A * 5/1999 Friemel ............... G01S 7/52074 600/443
2020/0273168 A1 8/2020 Izumi et al.
2022/0087652 A1* 3/2022 Takahashi ............ A61B 8/4254

FOREIGN PATENT DOCUMENTS

JP 7280711 B2 5/2023

* cited by examiner

*Primary Examiner* — Joel F Brutus
(74) *Attorney, Agent, or Firm* — Studebaker Brackett PLLC

(57) ABSTRACT

A probe position and posture information acquisition unit acquires position and posture information indicating a position and a posture of the ultrasound probe when each of the pieces of frame data for forming ultrasound volume data is acquired, and associates the position and posture information with each of the pieces of frame data. A volume data forming unit forms the ultrasound volume data by changing at least one of a perpendicular plane position, which is a position in a plane perpendicular to an arrangement direction of the pieces of frame data in a data space, or a posture of each of the pieces of frame data in accordance with the position and posture information associated with a corresponding piece of the frame data, and then arranging the pieces of frame data in the arrangement direction.

6 Claims, 12 Drawing Sheets

ULTRASOUND VOLUME DATA FORMING APPARATUS AND ULTRASOUND VOLUME DATA FORMING PROGRAM

This application claims priority to Japanese Patent Application No. 2024-135555 filed on Aug. 15, 2024 which is incorporated herein by reference in its entirety including the specification, claims, drawings, and abstract.

BACKGROUND OF THE INVENTION

1. Field of the Invention

The present specification discloses improvements in an ultrasound volume data forming apparatus and an ultrasound volume data forming program.

2. Description of the Related Art

In the related art, medical volume data is formed, and the medical volume data is used for various purposes. Volume data is data in which data elements called voxels are arranged in three dimensions. Each data element included in the medical volume data serves as a parameter representing a region (for example, a certain region including a tissue) in a subject. In the medical volume data, any cross section is set, and a two-dimensional image representing a cross section can be formed by extracting and reconstructing the medical volume data at the cross section. Such a two-dimensional image is used for diagnosis of a subject or the like.

As a type of medical volume data, ultrasound volume data has been known in the related art. The ultrasound volume data is formed based on a reception signal obtained by transmitting and receiving ultrasound to and from a subject. Each data element included in the ultrasound volume data serves as a parameter indicating, for example, an intensity of a reflected wave from the subject.

It is also possible to form ultrasound volume data by transmitting and receiving ultrasound to and from a subject using a two-dimensional array ultrasound probe in which ultrasound transducer elements that generate ultrasound are two-dimensionally arranged. However, in the related art, a method of forming ultrasound volume data using an ultrasound probe in which ultrasound transducer elements are arranged in one direction and which scans an ultrasound beam on a flat scanning plane has been proposed.

Specifically, a reception signal corresponding to each scanning plane (referred to as "frame data" in the present specification) is acquired while moving the ultrasound probe in a direction perpendicular to the scanning plane (referred to as "sweep" in the present specification). The frame data is data in which data elements indicating an intensity of a reflected wave from a subject are two-dimensionally arranged in accordance with the scanning plane. Then, in a data space, pieces of the frame data are arranged and combined in a direction (referred to as an "arrangement direction" in the present specification) perpendicular to a two-dimensional array direction of the data elements to form ultrasound volume data.

For example, JP7280711B discloses an ultrasound diagnostic apparatus that generates volume data based on a plurality of pieces of frame data acquired by transmitting and receiving ultrasound while sweeping an ultrasound probe, the ultrasound diagnostic apparatus comprising: a position sensor that acquires position information indicating a position of the ultrasound probe; a data acquisition function of associating the position information indicating the position of the ultrasound probe when the pieces of frame data are acquired with each piece of frame data, a smoothing processing function of smoothing a position deviation between the pieces of frame data based on the position information associated with each piece of frame data, and a volume generation circuit that generates ultrasound volume data based on a plurality of pieces of smoothed frame data.

SUMMARY OF THE INVENTION

In a case where the ultrasound volume data is formed by arranging the plurality of pieces of frame data in an arrangement direction, it is desirable that the position and a posture of the ultrasound probe when each piece of frame data is acquired are constant. The position of the ultrasound probe here means a position in a plane perpendicular to a sweep direction (referred to as a "perpendicular plane position" in the present specification), not a position in the sweep direction (referred to as a "sweep position" in the present specification). In the following description, in a case where the term "position" of an ultrasound probe 14 is simply referred to, the position is a concept that encompasses both the sweep position and the perpendicular plane position.

Since the perpendicular plane position and the posture of the ultrasound probe represent a perpendicular plane position and a posture of the scanning plane corresponding to the frame data, in a case where the perpendicular plane position or the posture of the ultrasound probe when each piece of frame data is acquired varies, the perpendicular plane positions and the postures of a plurality of scanning planes corresponding to a plurality of pieces of frame data for forming the ultrasound volume data also vary, and in a case where the ultrasound volume data is formed by arranging the plurality of pieces of frame data in the arrangement direction, it results in distortion in the ultrasound volume data. That is, accuracy of the ultrasound volume data is reduced.

It may be difficult to maintain the perpendicular plane position and the posture of the ultrasound probe in a constant manner when a plurality of pieces of frame data are acquired by sweeping the ultrasound probe, due to factors such as the fact that the ultrasound probe is swept by an operator (that is, a human) such as a doctor, a body surface of the subject to be swept by the ultrasound probe is not flat, and the body surface of the subject to be swept by the ultrasound probe may be soft (for example, a breast). As a result, the accuracy of the ultrasound volume data may be reduced.

An object of an ultrasound volume data forming apparatus disclosed in the present specification is to improve accuracy of ultrasound volume data formed by arranging a plurality of pieces of frame data.

An ultrasound volume data forming apparatus disclosed in the present specification comprises: a frame data sequence acquisition unit that acquires a frame data sequence acquired by sweeping an ultrasound probe that scans an ultrasound beam on a subject, in a direction perpendicular to a scanning plane of the ultrasound beam, the frame data sequence including each piece of frame data having a data element sequence, two-dimensionally arranged in accordance with the scanning plane, indicating a signal intensity of a reflected wave from the subject, in which position and posture information indicating a perpendicular plane position, which is a position of the ultrasound probe when a piece of the frame data in a plane perpendicular to a sweep direction is acquired, and a posture of the ultrasound probe when the piece of the frame data is acquired is associated with each piece of the frame data included in the frame data sequence;

and a volume data forming unit that forms ultrasound volume data by arranging the frame data sequence in an arrangement direction that is a direction perpendicular to a two-dimensional array direction of the data element sequence in a data space, the volume data forming unit forming the ultrasound volume data by changing at least one of a perpendicular plane position, which is a position in a plane perpendicular to the arrangement direction, or a posture of each piece of the frame data included in the frame data sequence in accordance with the position and posture information associated with the piece of frame data, and then arranging the pieces of the frame data in the arrangement direction.

The volume data forming unit may extract a first feature point in one piece of the frame data among adjacent pieces of the frame data in the frame data sequence and a second feature point corresponding to the first feature point in the other piece of the frame data, and change at least one of the perpendicular plane position or the posture of each piece of the frame data such that the first feature point and the second feature point are arranged in the arrangement direction.

The volume data forming unit may form the ultrasound volume data by excluding frame data in which at least one of the perpendicular plane position or the posture has an outlier compared to a plurality of other pieces of the frame data, based on the position and posture information associated with each piece of the frame data.

The volume data forming unit may generate, based on both pieces of the frame data adjacent to each other in the frame data sequence, intermediate frame data to be disposed between both pieces of the frame data, and form the ultrasound volume data by using the intermediate frame data.

The position and posture information may indicate a perpendicular plane position and a posture of the ultrasound probe relative to a body surface of the subject, based on a captured image acquired by imaging a probe detection marker attached to the ultrasound probe and on a body surface detection marker attached to the body surface of the subject, via a camera.

In addition, an ultrasound volume data forming program disclosed in the present specification causes a computer to function as: a frame data sequence acquisition unit that acquires a frame data sequence acquired by sweeping an ultrasound probe that scans an ultrasound beam on a subject, in a direction perpendicular to a scanning plane of the ultrasound beam, the frame data sequence including each piece of frame data having a data element sequence, two-dimensionally arranged in accordance with the scanning plane, indicating a signal intensity of a reflected wave from the subject, in which position and posture information indicating a perpendicular plane position, which is a position of the ultrasound probe when a piece of the frame data in a plane perpendicular to a sweep direction is acquired, and a posture of the ultrasound probe when the piece of the frame data is acquired is associated with each piece of the frame data included in the frame data sequence; and a volume data forming unit that forms ultrasound volume data by arranging the frame data sequence in an arrangement direction that is a direction perpendicular to a two-dimensional array direction of the data element sequence in a data space, the volume data forming unit forming the ultrasound volume data by changing at least one of a perpendicular plane position, which is a position in a plane perpendicular to the arrangement direction, or a posture of each piece of the frame data included in the frame data sequence in accordance with the position and posture information associated with the piece of frame data, and then arranging the pieces of the frame data in the arrangement direction.

With the ultrasound volume data forming apparatus disclosed in the present specification, it is possible to improve the accuracy of the ultrasound volume data formed by arranging a plurality of pieces of frame data.

DESCRIPTION OF THE PREFERRED EMBODIMENTS

Figure 1:
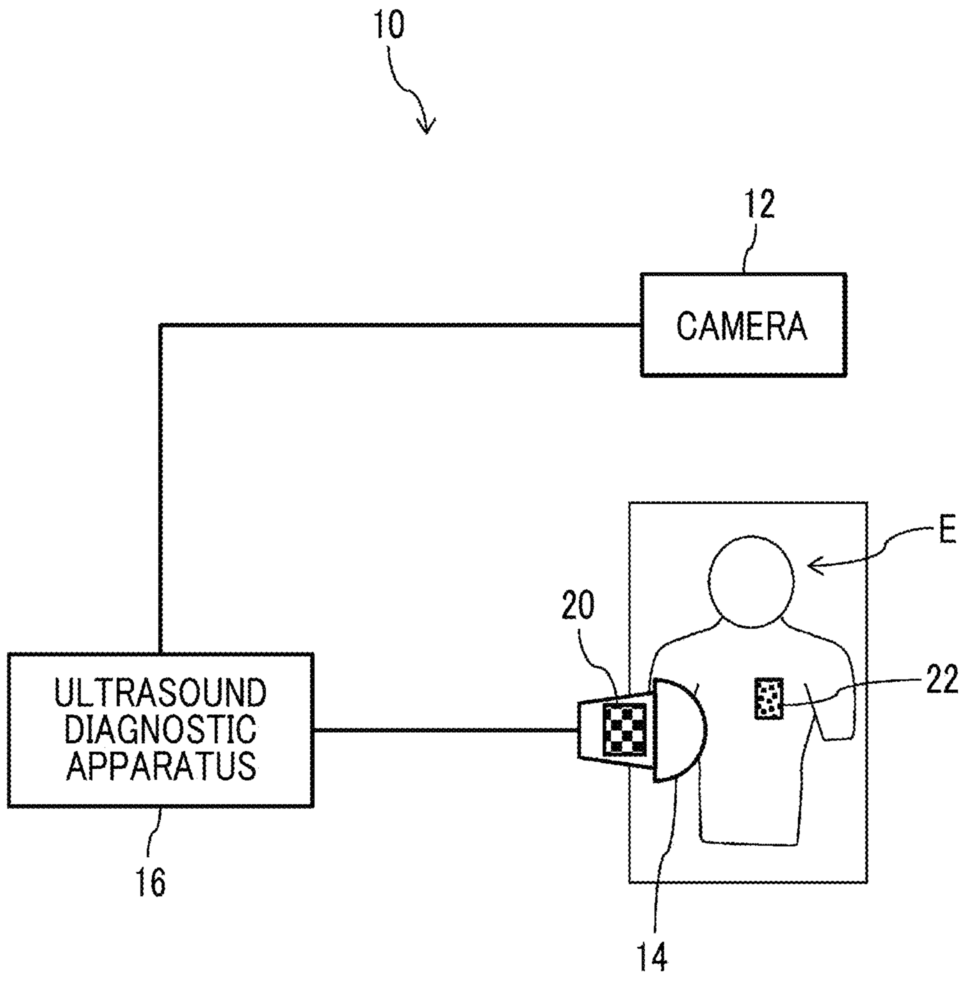
FIG. 1 is a schematic diagram showing a configuration of an ultrasound volume data forming system according to the present embodiment.

FIG. 1 is a schematic diagram of a configuration of an ultrasound volume data forming system 10 according to the present embodiment. The ultrasound volume data forming system 10 is configured to include a camera 12 and an ultrasound diagnostic apparatus 16 as an ultrasound volume data forming apparatus including an ultrasound probe 14. The camera 12 and the ultrasound diagnostic apparatus 16 are communicatively connected to each other.

In the present embodiment, a probe detection marker 20 is attached to the ultrasound probe 14. The probe detection marker 20 is a marker for detecting a position and a posture of the ultrasound probe 14. In addition, a body surface detection marker 22 is attached to a body surface of a subject E. The body surface detection marker 22 has a different pattern from the probe detection marker 20 and is a marker for detecting a position and a posture of the body surface of the subject E. An example of the probe detection marker 20 and the body surface detection marker 22 is an augmented reality (AR) marker.

The camera 12 is configured to include, in addition to a lens and an image sensor, a processor including a central processing unit (CPU) and the like, a communication interface including a network adapter and the like, and the like. The camera 12 images the ultrasound probe 14 (specifically, the probe detection marker 20) and the subject E (specifically, the body surface detection marker 22). A captured image is formed by the image sensor of the camera 12, and the captured image is transmitted to the ultrasound diagnostic apparatus 16 via the communication interface of the camera 12.

Figure 2:
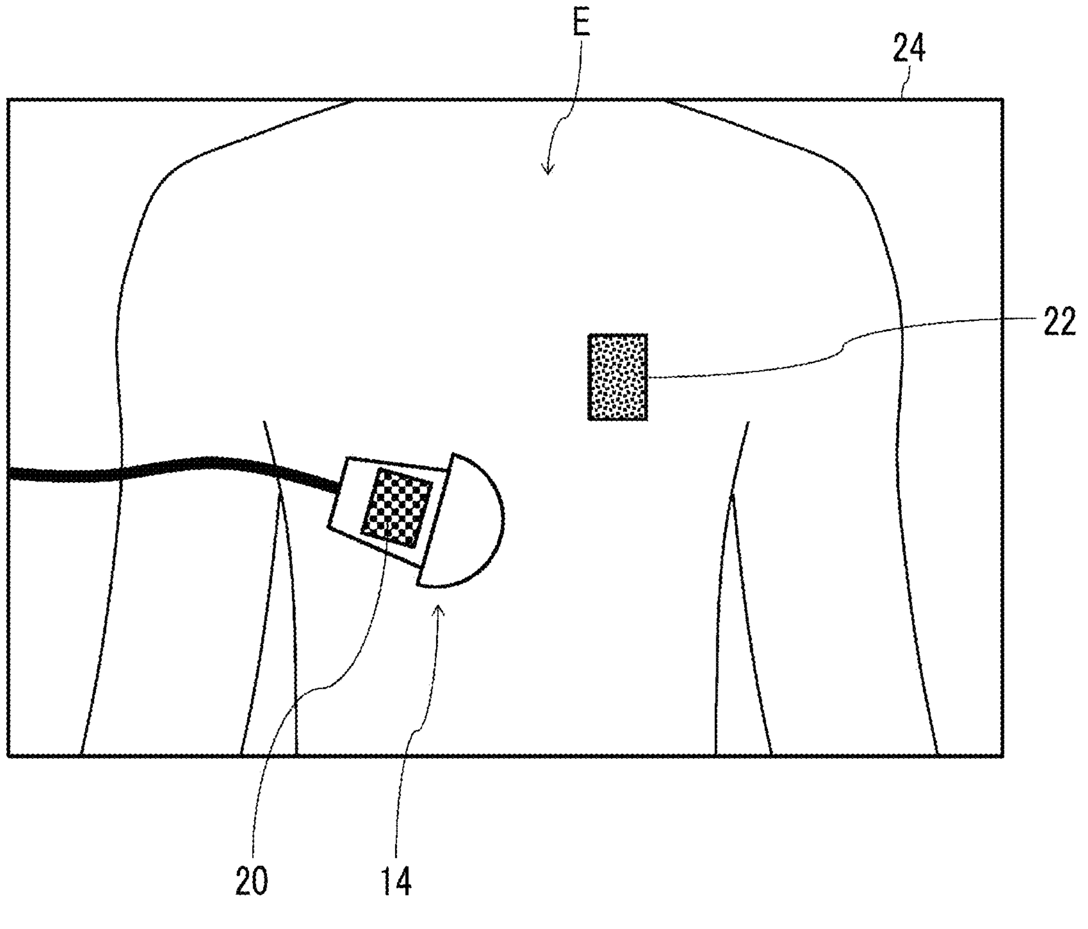
FIG. 2 is a diagram showing an example of a captured image of a camera.

FIG. 2 is a diagram showing an example of a captured image 24 of the camera 12. As described above, the captured image 24 includes images of the probe detection marker 20 and the body surface detection marker 22. The ultrasound diagnostic apparatus 16 can detect the position and the posture of the ultrasound probe 14 by analyzing the image of the probe detection marker 20 shown in the captured image 24. Further, the ultrasound diagnostic apparatus 16 can detect the position and the posture of the body surface of the subject E by analyzing the image of the body surface detection marker 22 shown in the captured image 24. Details of processing of detecting the positions and postures of the ultrasound probe 14 and the subject E will be described below.

Figure 3:
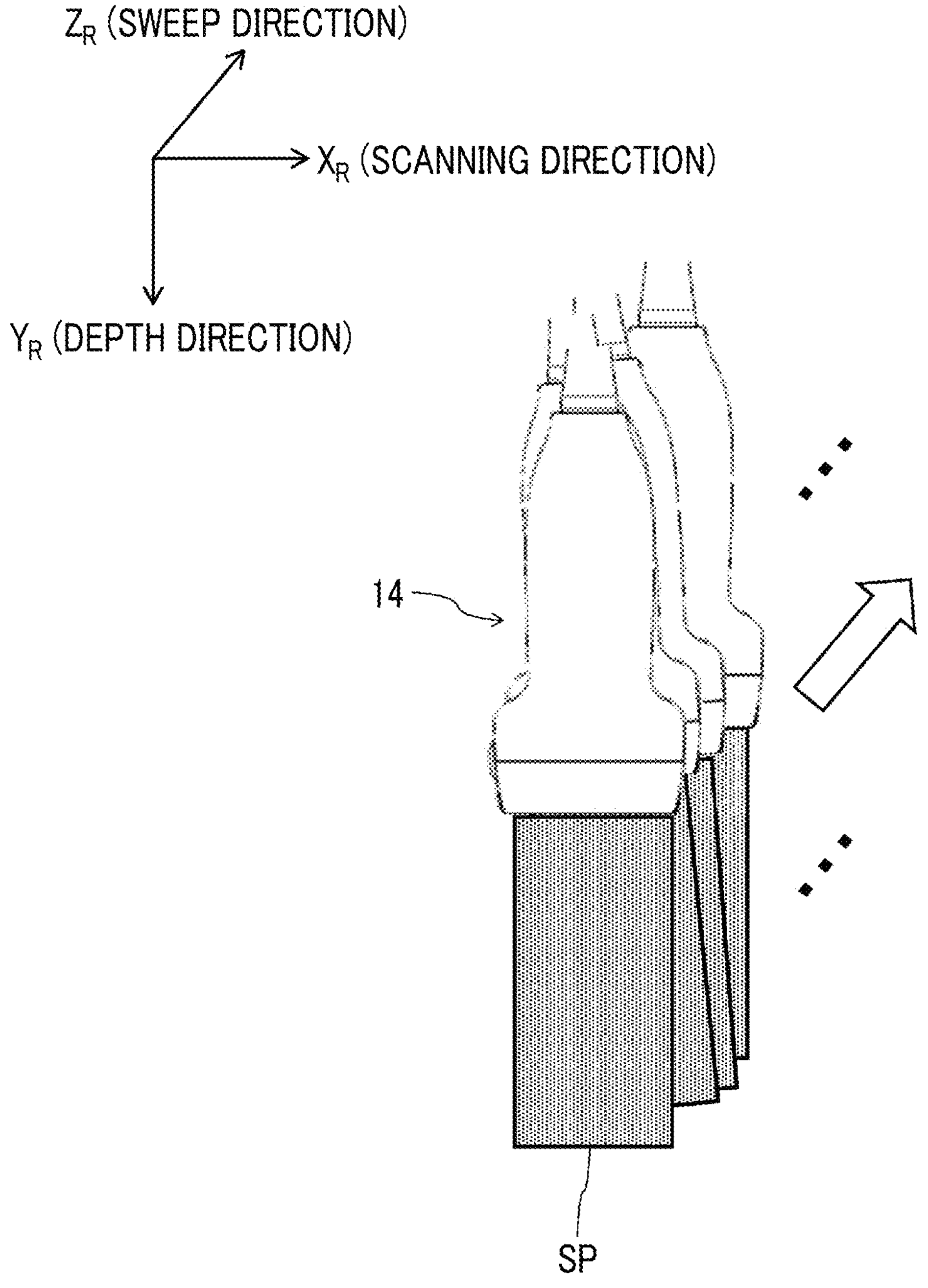
FIG. 3 is a diagram showing a plurality of scanning planes corresponding to a plurality of pieces of frame data for forming ultrasound volume data.

The ultrasound diagnostic apparatus 16 as the ultrasound volume data forming apparatus forms ultrasound volume data. FIG. 3 is a diagram showing a plurality of scanning planes SP corresponding to a plurality of pieces of frame data for forming the ultrasound volume data. In the drawings referred to in the present specification, a scanning direction (in particular, a scanning direction when first frame data among a plurality of frames for forming ultrasound volume data is acquired) of an ultrasound beam emitted from the ultrasound probe 14 in a horizontal direction is defined as an $X_R$ axis, a depth direction of the subject E is defined as a $Y_R$ axis, and a horizontal direction perpendicular to the $X_R$ axis and the $Y_R$ axis is defined as a $Z_R$ axis. The $X_R$ axis, the $Y_R$ axis, and the $Z_R$ axis are axes representing a real space.

An operator of the ultrasound diagnostic apparatus 16, such as a doctor, moves the ultrasound probe 14 in a sweep direction (that is, a $Z_R$-axis direction), which is a direction perpendicular to a scanning plane SP (that is, an $X_RY_R$ plane), while bringing the ultrasound probe 14 into contact with the subject E to form a plurality of pieces of frame data corresponding to each of the scanning planes SP aligned along the sweep direction. As shown in FIG. 3, in a case where the ultrasound probe 14 is swept to form the plurality of pieces of frame data, a perpendicular plane ($X_RY_R$ plane) position or posture (that is, a perpendicular plane position or posture of the scanning plane SP) of the ultrasound probe 14 may vary. The ultrasound diagnostic apparatus 16 forms ultrasound volume data by combining the plurality of pieces of frame data corresponding to the plurality of scanning planes SP. In particular, the ultrasound diagnostic apparatus 16 forms the ultrasound volume data so as to suppress a decrease in accuracy even in a case where the perpendicular plane position or the posture of the plurality of scanning planes SP varies. Details of processing of forming the ultrasound volume data will be described below.

Figure 4:
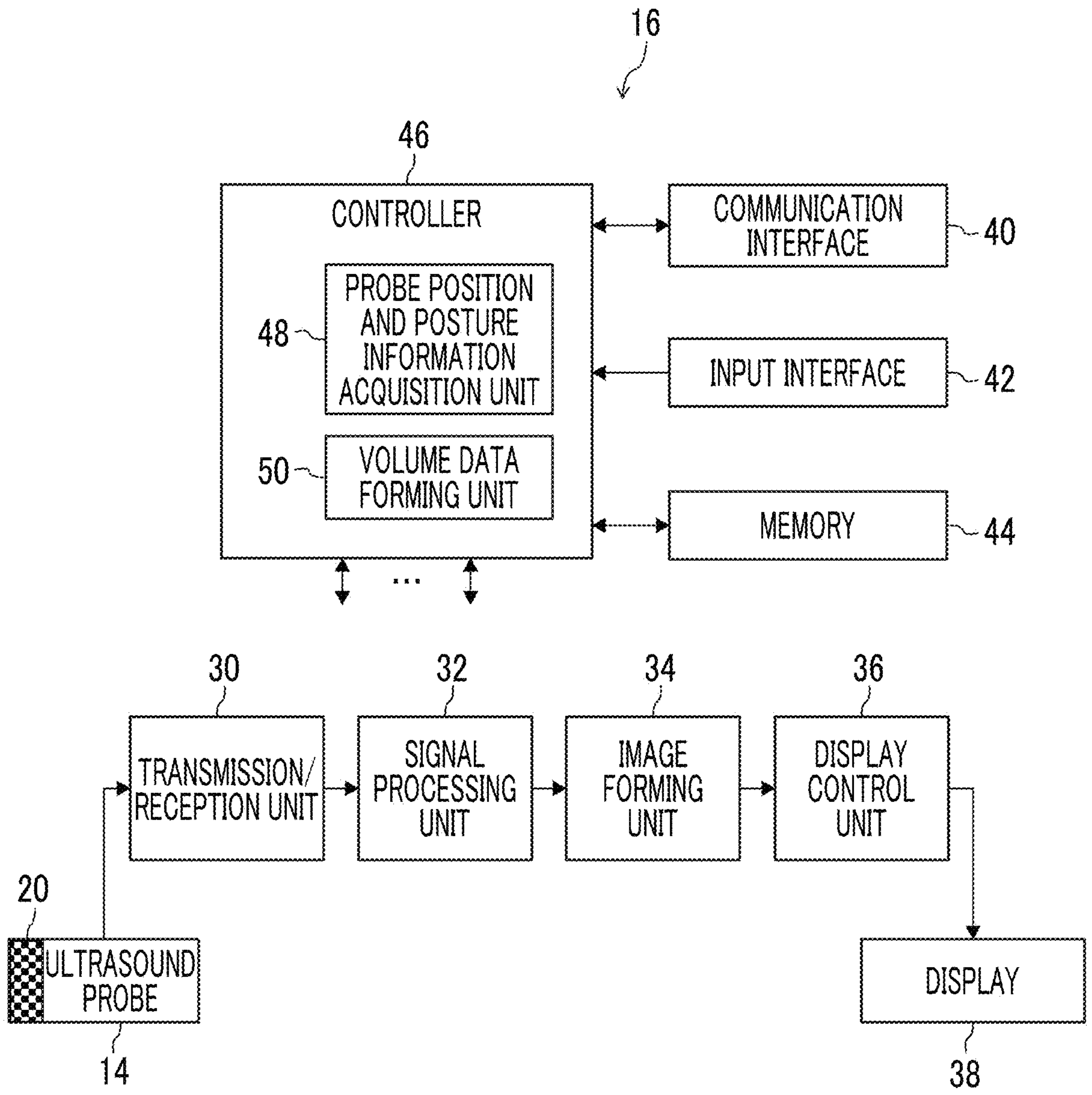
FIG. 4 is a schematic diagram of a configuration of an ultrasound diagnostic apparatus according to the present embodiment.

FIG. 4 is a schematic diagram of a configuration of the ultrasound diagnostic apparatus 16. The ultrasound diagnostic apparatus 16 is a medical apparatus installed in medical institutions such as a hospital.

The ultrasound probe 14 is a device that transmits and receives ultrasound to and from the subject E. The ultrasound probe 14 includes a transducer element array including a plurality of transducer elements that transmit and receive ultrasound to and from the subject E. The transducer element array is formed of the plurality of transducer elements arranged in one direction (array direction). In a case where a transmission signal is supplied to each transducer element from a transmission/reception unit 30, which will be described later, each transducer element generates ultrasound. Specifically, the ultrasound probe 14 scans an ultrasound beam in a plane (scanning plane SP) parallel to the array direction.

As described above, the probe detection marker 20 is attached to the ultrasound probe 14.

The transmission/reception unit 30 transmits a transmission signal to the ultrasound probe 14 (specifically, each transducer element of the transducer element array) under control of a controller 46, which will be described later. As a result, the ultrasound beam is scanned by the ultrasound probe 14 on the scanning plane SP. Additionally, the transmission/reception unit 30 receives a reception signal from each transducer element that has received a reflected wave from the subject E. The transmission/reception unit 30 includes an adder and a plurality of delay devices corresponding to the respective transducer elements and performs phase alignment and addition processing of aligning and adding phases of the reception signals from the transducer elements by using the adder and the plurality of delay devices. As a result, a reception beam signal in which information indicating a signal intensity of the reflected wave from the subject E is arranged in the depth direction of the subject E is formed. A plurality of reception beam signals corresponding to one scanning plane SP constitute frame data.

As the operator moves the ultrasound probe 14 in the sweep direction, a frame data sequence including the plurality of pieces of frame data corresponding to each scanning plane SP (see FIG. 3) is acquired. A movement path of the scanning plane SP, which moves as the ultrasound probe 14 is swept, may include, for example, a target tissue of the subject E that is to be examined or treated. Each piece of frame data has a data element sequence, two-dimensionally arranged in accordance with the scanning plane SP, indicating the signal intensity of the reflected wave from the subject E. As described above, in the present embodiment, the transmission/reception unit 30 exhibits a function as a frame data sequence acquisition unit.

A signal processing unit 32 performs various types of signal processing including filter processing of applying a bandpass filter, detection processing, and the like, on the reception beam signal from the transmission/reception unit 30.

An image forming unit 34 forms an ultrasound tomographic image (B-mode image) representing a cross section (particularly, the scanning plane SP of the ultrasound beam) of the subject E based on the reception beam signal subjected to the signal processing in the signal processing unit 32. In addition, the image forming unit 34 forms a reconstructed ultrasound image by extracting and reconstructing ultrasound volume data formed as described below at any cross section.

A display control unit 36 performs control to display various images including the ultrasound tomographic image or the reconstructed ultrasound image formed by the image forming unit 34 on a display 38.

The display 38 as a display unit is, for example, a display device configured using a liquid-crystal display, an organic electroluminescence (EL), or the like.

The transmission/reception unit 30, the signal processing unit 32, the image forming unit 34, and the display control unit 36 included in the ultrasound diagnostic apparatus 16 are configured by a processor. The processor is configured to include at least one of a general-purpose processing device (for example, a CPU or the like) or a dedicated processing device (for example, a graphics processing unit (GPU), an application-specific integrated circuit (ASIC), a field-programmable gate array (FPGA), or a programmable logic device). The processor need not be configured using a single processing device but rather may be configured through cooperation of a plurality of processing devices that are present at physically separated positions. Additionally, each of the above-described units may be implemented through cooperation of hardware, such as a processor, and software.

A communication interface 40 is configured using, for example, a network adapter. The communication interface 40 exhibits a function of communicating with another device (particularly, the camera 12). In particular, the communication interface 40 receives the captured image 24 from the camera 12.

An input interface 42 is configured using, for example, a button, a trackball, or a touch panel. The input interface 42 is used to input an instruction of an operator who uses the ultrasound diagnostic apparatus 16 to the ultrasound diagnostic apparatus 16.

A memory 44 is configured to include a hard disk drive (HDD), a solid-state drive (SSD), an embedded MultiMediaCard (eMMC), a read-only memory (ROM), a random-access memory (RAM), or the like. The memory 44 stores an ultrasound volume data forming program for operating each unit of the ultrasound diagnostic apparatus 16. The ultrasound volume data forming program can also be stored in, for example, a computer-readable non-transitory storage medium such as a Universal Serial Bus (USB) memory or a CD-ROM. The ultrasound diagnostic apparatus 16 can read and execute the ultrasound volume data forming program from such a storage medium. Since the ultrasound diagnostic apparatus 16 reads the ultrasound volume data forming program to exhibit the functions described below, the ultrasound diagnostic apparatus 16 can be said to be a computer program product.

The controller 46 includes at least one of a general-purpose processor (such as a CPU) or a dedicated processor (such as a GPU, an ASIC, an FPGA, or a programmable logic device). The controller 46 need not be configured using a single processing device but rather may be configured through cooperation of a plurality of processing devices that are present at physically separated positions. The controller 46 controls each unit of the ultrasound diagnostic apparatus 16. In addition, as shown in FIG. 4, the controller 46 exhibits functions as a probe position and posture information acquisition unit 48 and a volume data forming unit 50 in accordance with the ultrasound volume data forming program stored in the memory 44.

The probe position and posture information acquisition unit 48 acquires position and posture information indicating the position (perpendicular plane position and sweep position) and the posture of the ultrasound probe 14. In particular, the probe position and posture information acquisition unit 48 acquires the position and posture information indicating the position and posture of the ultrasound probe 14 when each piece of frame data for forming the ultrasound volume data is acquired.

In the present embodiment, the probe position and posture information acquisition unit 48 acquires the position and posture information by analyzing the captured image 24 acquired by the camera 12 to detect the position and the posture of the ultrasound probe 14. As described above, the captured image 24 includes the image of the probe detection marker 20 for detecting the position and the posture of the ultrasound probe 14 (see FIG. 2). The probe position and posture information acquisition unit 48 acquires the position and posture information by analyzing the image of the probe detection marker 20 in the captured image 24. The position of the ultrasound probe 14 may be expressed by, for example, three-dimensional coordinates in a camera coordinate system. The posture of the ultrasound probe 14 may be expressed by, for example, a rotation angle with respect to each of three predetermined orthogonal axes in the camera coordinate system. Since a known method can be used as a method of detecting the position and the posture of the ultrasound probe 14 in the camera coordinate system from the image of the probe detection marker 20 included in the captured image 24, detailed descriptions thereof will be omitted here.

As described above, the captured image 24 also includes the image of the body surface detection marker 22 for detecting the position and the posture of the body surface of the subject E (see FIG. 2). The probe position and posture information acquisition unit 48 may detect the position and the posture of the body surface of the subject E by analyzing the image of the body surface detection marker 22 in the captured image 24. In addition, the probe position and posture information acquisition unit 48 may detect a position and a posture of the ultrasound probe 14 relative to the position and the posture of the body surface of the subject E. As a result, the position and the posture of the ultrasound probe 14 with respect to the subject E, which absorb any variation in the position or the posture of the subject E, can be obtained.

The probe position and posture information acquisition unit 48 may detect the position and the posture of the ultrasound probe 14 by a method other than analyzing the captured image 24. For example, a position and posture sensor such as a magnetic sensor or an acceleration sensor may be provided in the ultrasound probe 14, and the position and the posture of the ultrasound probe 14 may be detected based on a detection value of the position and posture sensor.

The position and the posture of the scanning plane SP (see FIG. 3) are determined by the position and the posture of the ultrasound probe 14. Therefore, it can be said that the position and posture information acquired by the probe position and posture information acquisition unit 48 indicates the position and posture of the scanning plane SP corresponding to each piece of frame data for forming the ultrasound volume data.

The probe position and posture information acquisition unit 48 stores the frame data acquired by the transmission/reception unit 30 in the memory 44 in association with the position and posture information indicating the position and the posture of the ultrasound probe 14 when the frame data is acquired. As a result, the frame data sequence including the plurality of pieces of frame data, each of which is associated with the position and posture information, is stored in the memory 44.

Figure 5:
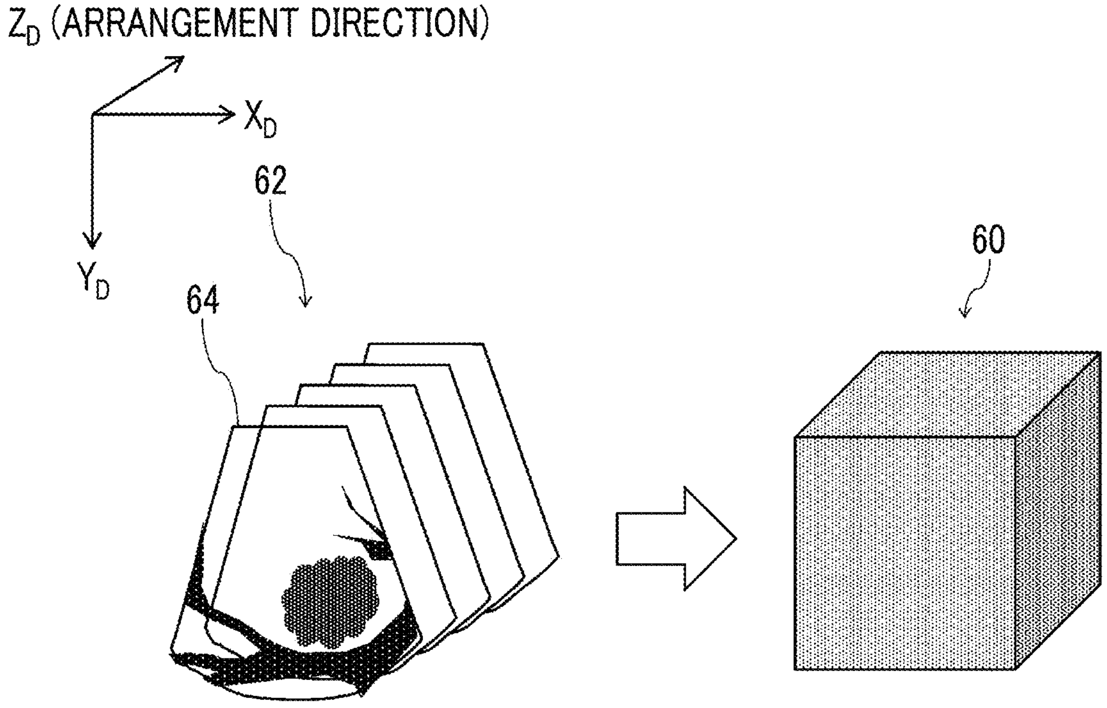
FIG. 5 is a conceptual diagram showing a concept of processing of forming ultrasound volume data.

The volume data forming unit 50 forms ultrasound volume data based on the above-described frame data sequence. FIG. 5 is a conceptual diagram showing a concept of processing of forming ultrasound volume data 60. In FIG. 5, an $X_D$-axis direction, a $Y_D$-axis direction, and a $Z_D$-axis direction, which are orthogonal to each other in a data space in which the ultrasound volume data 60 is defined, are shown. The volume data forming unit 50 forms the ultrasound volume data 60 by arranging pieces of frame data 64 in an arrangement direction (in the example of FIG. 5, the $Z_D$-axis direction) that is a direction perpendicular to a two-dimensional array direction (in the example of FIG. 5, the $X_D$-axis and $Y_D$-axis directions) of the data element sequence included in each piece of the frame data 64. A position of each piece of the frame data 64 in the arrangement direction may be determined based on the sweep position of the ultrasound probe 14 included in the position and posture information associated with each piece of the frame data 64.

The frame data 64 may be a plurality of reception beam signals corresponding to a single scanning plane SP, formed by the transmission/reception unit 30 (or a plurality of reception beam signals processed by the signal processing unit 32), or may be a single ultrasound tomographic image formed by the image forming unit 34 based on the plurality of reception beam signals.

Since a known method can be used as a method of forming the ultrasound volume data 60 from a frame data sequence 62, detailed descriptions thereof will be omitted here.

As described above, since the target tissue of the subject E is included in the movement path of the scanning plane SP, the ultrasound volume data 60 is data including the target tissue of the subject E. In a case where the ultrasound volume data 60 is formed, any cross section is set in the ultrasound volume data 60 by the operator or the like, and the image forming unit 34 can form a reconstructed ultrasound image showing the target tissue by extracting and reconstructing the ultrasound volume data 60 at the set cross section.

Here, a case where at least one of the perpendicular plane position or the posture of the ultrasound probe 14 is changed while the ultrasound probe 14 is swept to acquire the frame data sequence 62 is considered (see FIG. 3). In such a case, the volume data forming unit 50 forms the ultrasound volume data 60 by changing at least one of a perpendicular plane position, which is a position in a plane ($X_DY_D$ plane) perpendicular to the arrangement direction ($Z_D$-axis direction), or a posture of each piece of the frame data 64 included in the frame data sequence 62 in accordance with the position and posture information associated with the frame data 64, and then arranging the pieces of the frame data 64 in the arrangement direction.

Figure 6:
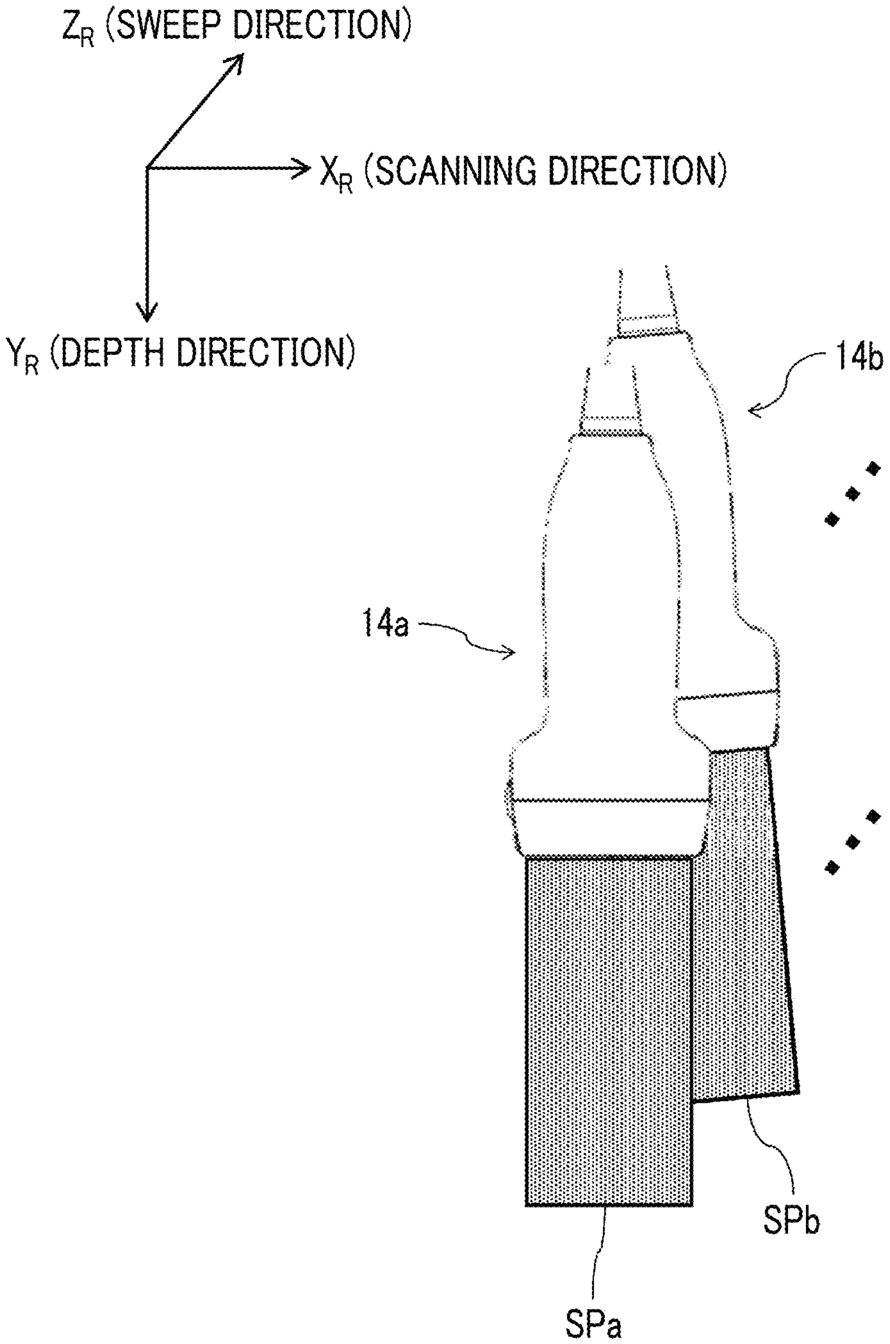
FIG. 6 is a diagram showing an ultrasound probe at a first sweep position and a second sweep position.

Hereinafter, a detailed description will be provided with reference to FIG. 6 and subsequent figures. FIG. 6 is a diagram showing the ultrasound probe 14 at a first sweep position 14*a* and a second sweep position 14*b*. It is assumed that at least one of a perpendicular plane position or a posture of the ultrasound probe 14 (referred to as a "second position and posture" in the present specification) at the second sweep position 14*b* varies relative to a perpendicular plane position and a posture of the ultrasound probe 14 (referred to as a "first position and posture" in the present specification) at the first sweep position 14*a*. That is, it is assumed that at least one of a perpendicular plane position or a posture of a scanning plane SPb at the second sweep position 14*b* varies relative to a perpendicular plane position and a posture of a scanning plane SPa at the first sweep position 14*a*. In the following description, focus is placed on first frame data 64*a* corresponding to the scanning plane SPa and second frame data 64*b* (see FIGS. 7 and 8) corresponding to the scanning plane SPb, but the volume data forming unit 50 also performs the same processing between adjacent pieces of the frame data 64 in the frame data sequence 62.

Figure 7:
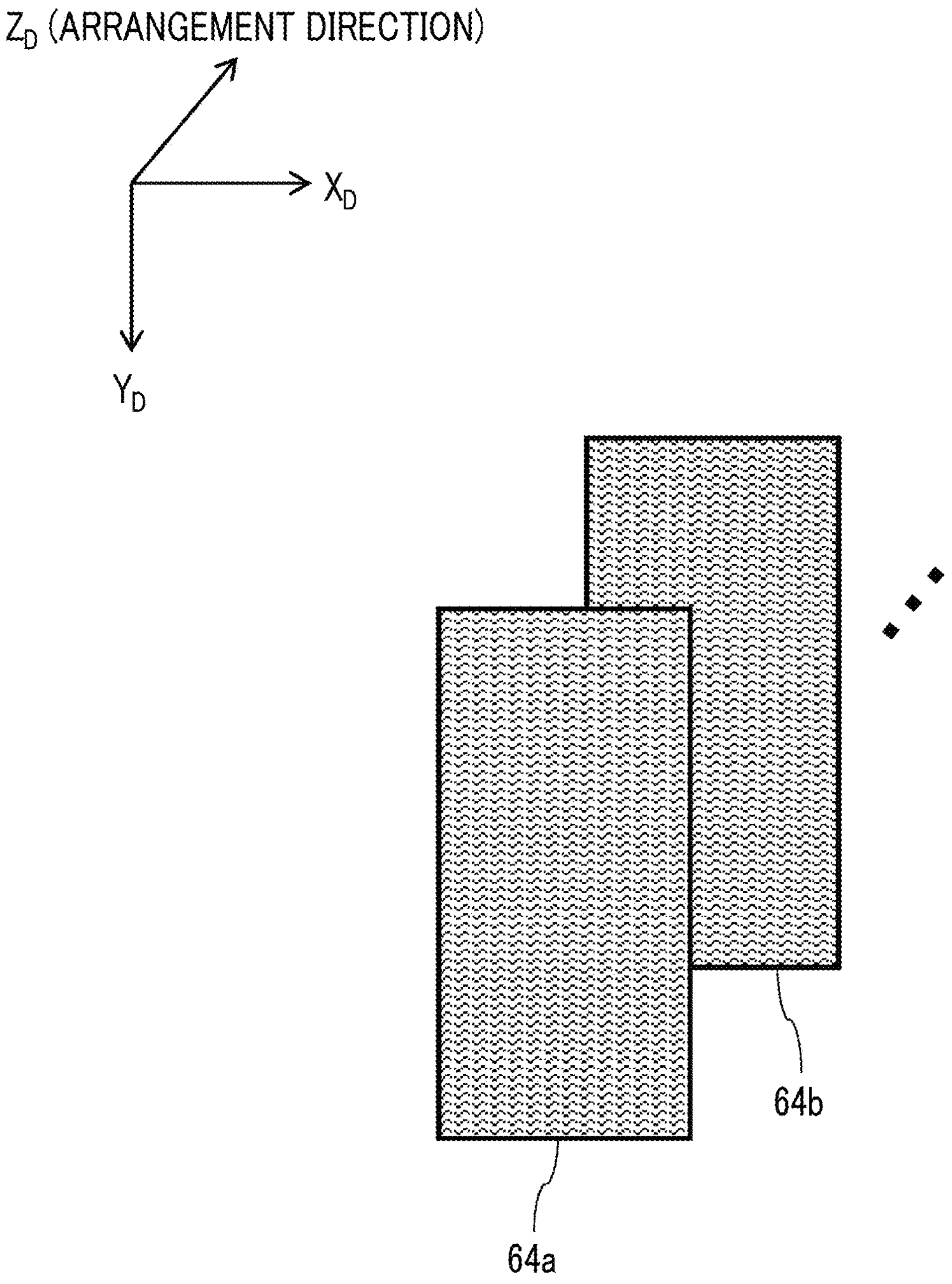
FIG. 7 is a first diagram showing first frame data and second frame data arranged in a data space.

FIG. 7 is a first diagram showing the first frame data 64*a* and the second frame data 64*b* arranged in the data space. Since the first position and posture and the second position and posture are different from each other, the perpendicular plane position and the posture between the scanning plane SPa and the scanning plane SPb are also different from each other. As shown in FIG. 7, in a case where the first frame data 64*a* and the second frame data 64*b* are disposed at the same perpendicular plane position and the same posture, a relationship of the perpendicular plane position and the posture between the first frame data 64*a* and the second frame data 64*b* is different from a relationship of the perpendicular plane position and the posture between the scanning plane SPa and the scanning plane SPb. Therefore, distortion occurs in the formed ultrasound volume data 60.

Figure 8:
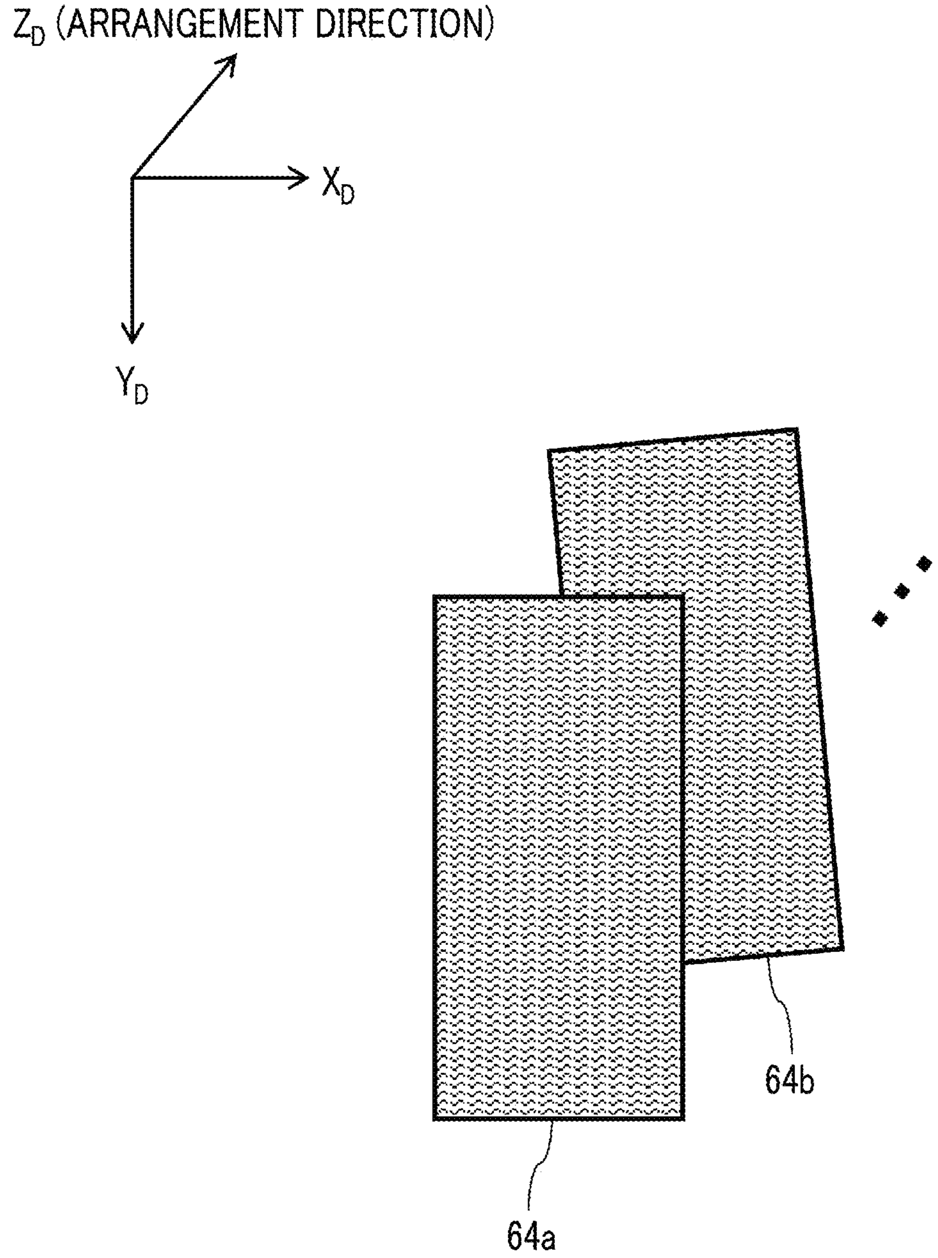
FIG. 8 is a second diagram showing the first frame data and the second frame data arranged in the data space.

Therefore, as shown in FIG. 8, the volume data forming unit 50 changes at least one of the perpendicular plane position or the posture of the first frame data 64*a* or the second frame data 64*b* such that the relationship of the perpendicular plane position and the posture between the first frame data 64*a* and the second frame data 64*b* is the same as the relationship between the first position and the second position (in other words, the relationship of the perpendicular plane position and the posture between the scanning plane SPa and the scanning plane SPb). Then, the first frame data 64*a* and the second frame data 64*b* (further, other frame data) are combined to form the ultrasound volume data 60.

As described above, by changing at least one of the perpendicular plane position or the posture of the first frame data 64*a* or the second frame data 64*b* so as to be the same as the relationship between the first position posture and the second position posture, the relationship of the perpendicular plane position and the posture between the first frame data 64*a* and the second frame data 64*b* is the same as the relationship of the perpendicular plane position and the posture between the scanning plane SPa and the scanning plane SPb, so that a distortion amount of the ultrasound volume data 60 to be formed can be reduced, that is, the accuracy of the ultrasound volume data 60 can be improved.

The volume data forming unit 50 may further extract, after changing at least one of the perpendicular plane position or the posture of the frame data as described above, a first feature point in one piece of the frame data 64 among adjacent pieces of the frame data 64 in the frame data sequence 62 and a second feature point corresponding to the first feature point in the other piece of the frame data 64, and change (further perform fine adjustment on) at least one of the perpendicular plane position or the posture of each piece of the frame data such that the first feature point and the second feature point are arranged in the arrangement direction.

Figure 9:
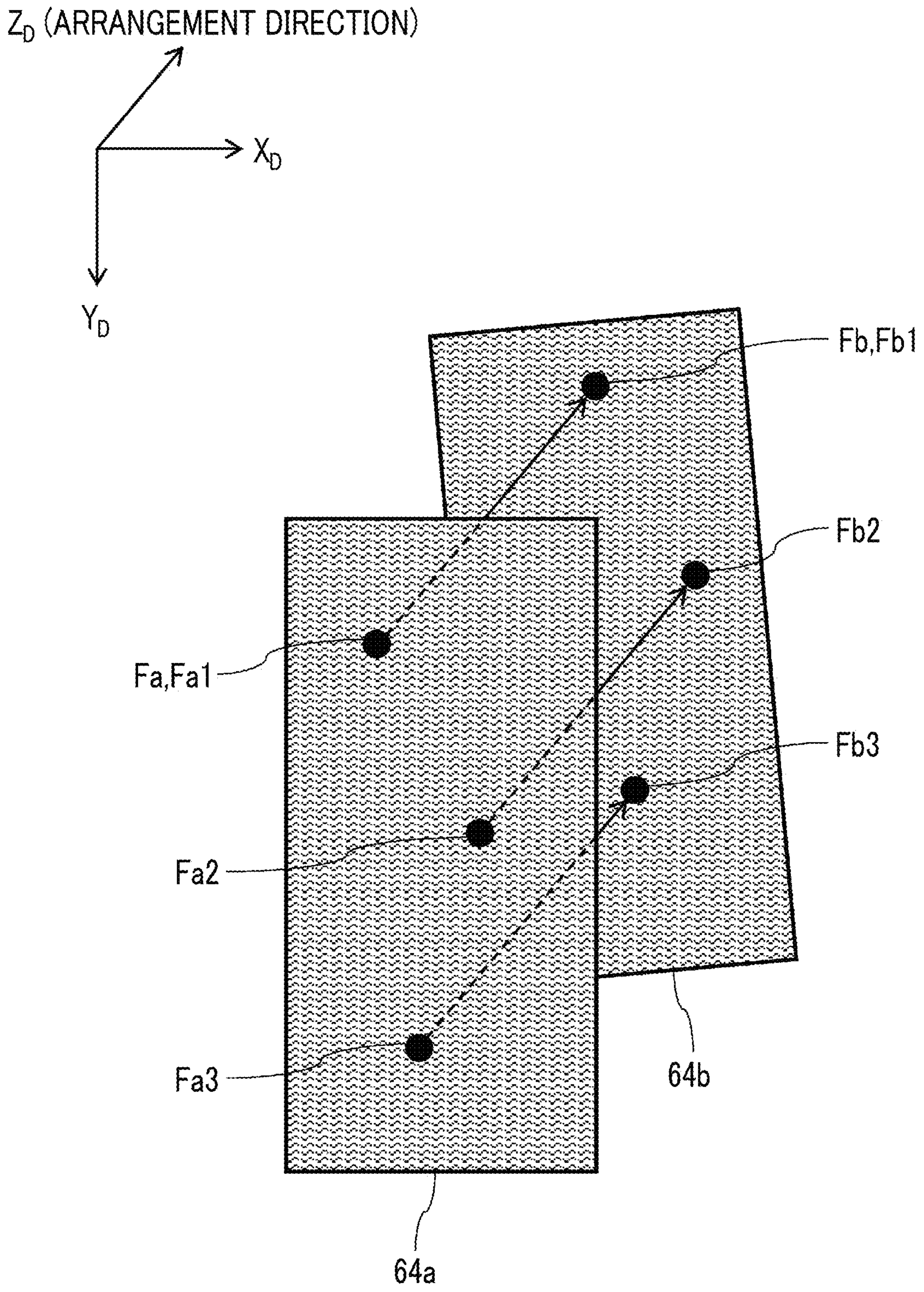
FIG. 9 is a diagram showing first feature points in the first frame data and second feature points in the second frame data.

FIG. 9 is a diagram showing first feature points Fa in the first frame data 64*a* and second feature points Fb in the second frame data 64*b*. Here, the description focuses on the first frame data 64*a* and the second frame data 64*b*, but the volume data forming unit 50 can also perform the same processing between adjacent pieces of the frame data 64 in the frame data sequence 62.

First, the volume data forming unit 50 detects the first feature point Fa from the first frame data 64*a*. Such detection processing can be performed on the ultrasound tomographic image, which is the first frame data 64*a*, using a technique such as scale-invariant feature transform (SIFT) or speeded-up robust features (SURF). The volume data forming unit 50 may detect a plurality of the first feature points Fa from the first frame data 64*a*. Similarly, the volume data forming unit 50 may detect the second feature point Fb from the second frame data 64*b*. A plurality of the second feature points Fb may also be detected from the second frame data 64*b*.

Next, in a case where the plurality of first feature points Fa and the plurality of second feature points Fb are detected, the volume data forming unit 50 specifies the second feature points Fb corresponding to the first feature points Fa. Since the relationship of the perpendicular plane position and the posture between the first frame data 64$a$ and the second frame data 64$b$ based on the position and posture information of the ultrasound probe 14 is changed prior to the detection of the first feature points Fa and the second feature points Fb, coordinates ($x_{d2}$, $y_{d2}$) of the second feature point Fb corresponding to a certain first feature point Fa in the $X_DY_D$ plane are often in the vicinity of coordinates ($x_{d1}$, $y_{d1}$) of the first feature point Fa in the $X_DY_D$ plane. Therefore, the volume data forming unit 50 can specify that the first feature point Fa and the second feature point Fb having coordinates close to each other in the $X_DY_D$ plane correspond to each other. Alternatively, the volume data forming unit 50 may specify the second feature point Fb corresponding to the first feature point Fa by comparing a pixel value of a pixel around the first feature point Fa with a pixel value of a pixel around the second feature point Fb, or the like. In the example of FIG. 9, a second feature point Fb1 corresponding to a first feature point Fa1 is specified, a second feature point Fb2 corresponding to a first feature point Fa2 is specified, and a second feature point Fb3 corresponding to a first feature point Fa3 is specified.

Then, the volume data forming unit 50 changes at least one of the perpendicular plane position or the posture of the first frame data 64$a$ or the second frame data 64$b$ such that the first feature point Fa and the second feature point Fb corresponding to each other are arranged in the arrangement direction ($Z_D$-axis direction). In other words, at least one of the perpendicular plane position or the posture of the first frame data 64$a$ or the second frame data 64$b$ is changed such that an error (a distance in the $X_DY_D$ plane) between the coordinates ($x_{d1}$, $y_{d1}$) of the first feature point Fa in the $X_DY_D$ plane and the coordinates ($x_{d2}$, $y_{d2}$) of the second feature point Fb in the $X_DY_D$ plane is less than a predetermined error threshold (ideally, such that the coordinates coincide). As shown in FIG. 9, in a case where the plurality of first feature points Fa and the plurality of second feature points Fb are detected, the volume data forming unit 50 changes at least one of the perpendicular plane position or the posture of the first frame data 64$a$ or the second frame data 64$b$ such that corresponding feature points, that is, the first feature point Fa1 and the second feature point Fb1, the first feature point Fa2 and the second feature point Fb2, and the first feature point Fa3 and the second feature point Fb3, are arranged in the arrangement direction.

As described above, by performing the fine adjustment based on the first feature point Fa and the second feature point Fb, the distortion amount of the formed ultrasound volume data 60 can be further reduced, that is, the accuracy of the ultrasound volume data 60 can be further improved.

Figure 10:
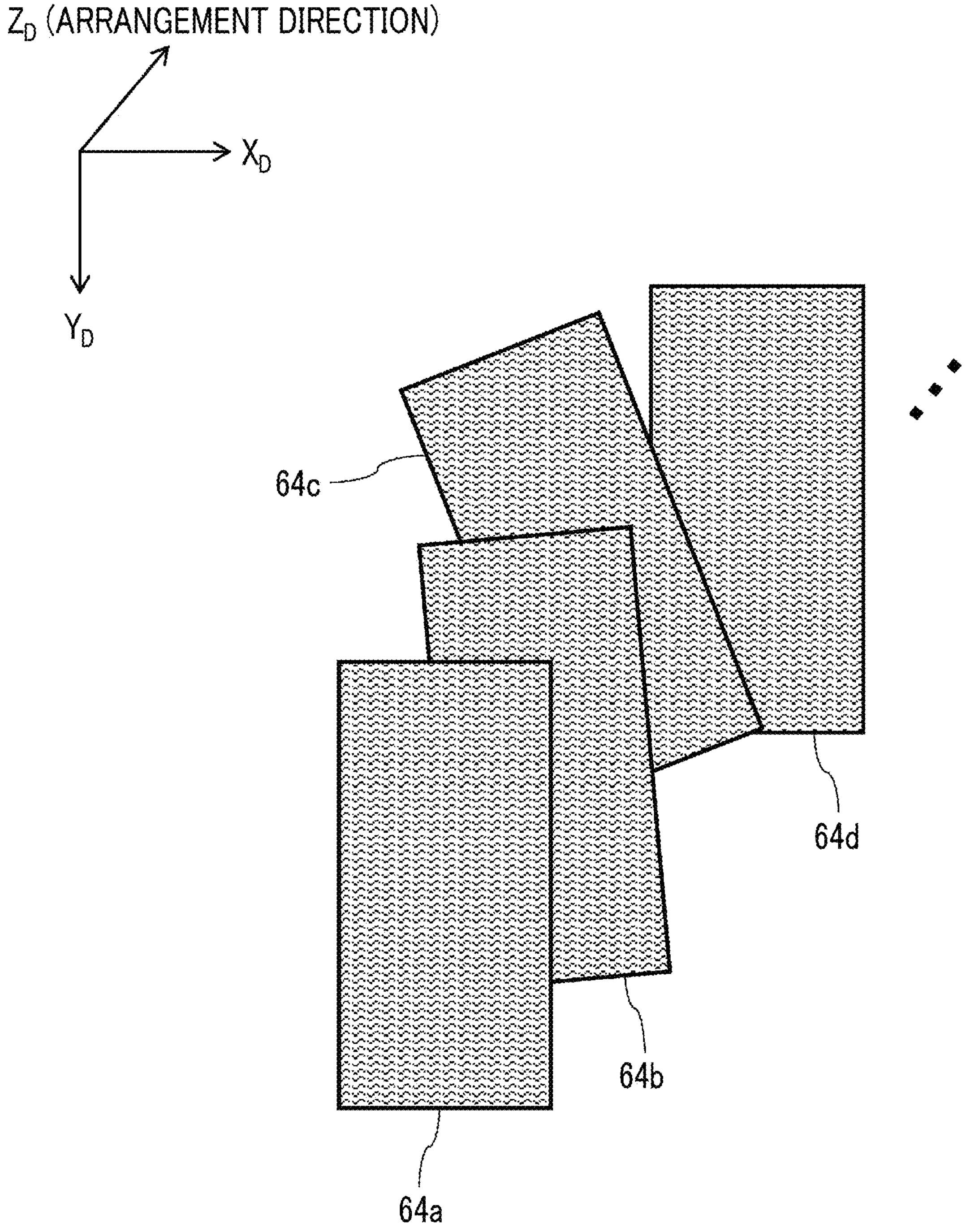
FIG. 10 is a diagram showing frame data with which outlier probe position and posture information is associated.

FIG. 10 is a diagram showing frame data 64$c$ with which outlier probe position and posture information is associated. In a case where the ultrasound probe 14 is swept to form a plurality of pieces of frame data, the perpendicular plane position or the posture of the ultrasound probe 14 may significantly vary due to certain factors. In such a case, as described above, in a case where at least one of the perpendicular plane position or the posture of each piece of the frame data 64 is changed in accordance with the position and posture information associated with the frame data 64, frame data 64, such as frame data 64$c$ shown in FIG. 10, may be generated, in which at least one of the perpendicular plane position or the posture is significantly different (that is, becomes an outlier) from the other pieces of frame data 64$a$, 64$b$, and 64$d$. From the viewpoint of suppressing a decrease in the accuracy of the ultrasound volume data 60, the ultrasound volume data 60 may be formed by excluding the frame data 64 in which at least one of the perpendicular plane position or the posture has an outlier compared to a plurality of the other pieces of the frame data 64.

Therefore, the volume data forming unit 50 may form the ultrasound volume data 60 by excluding the frame data 64 (the frame data 64$c$ in the example of FIG. 10) in which at least one of the perpendicular plane position or the posture has an outlier compared to a plurality of the other pieces of the frame data 64, based on the position and posture information associated with each piece of the frame data 64.

Figure 11:
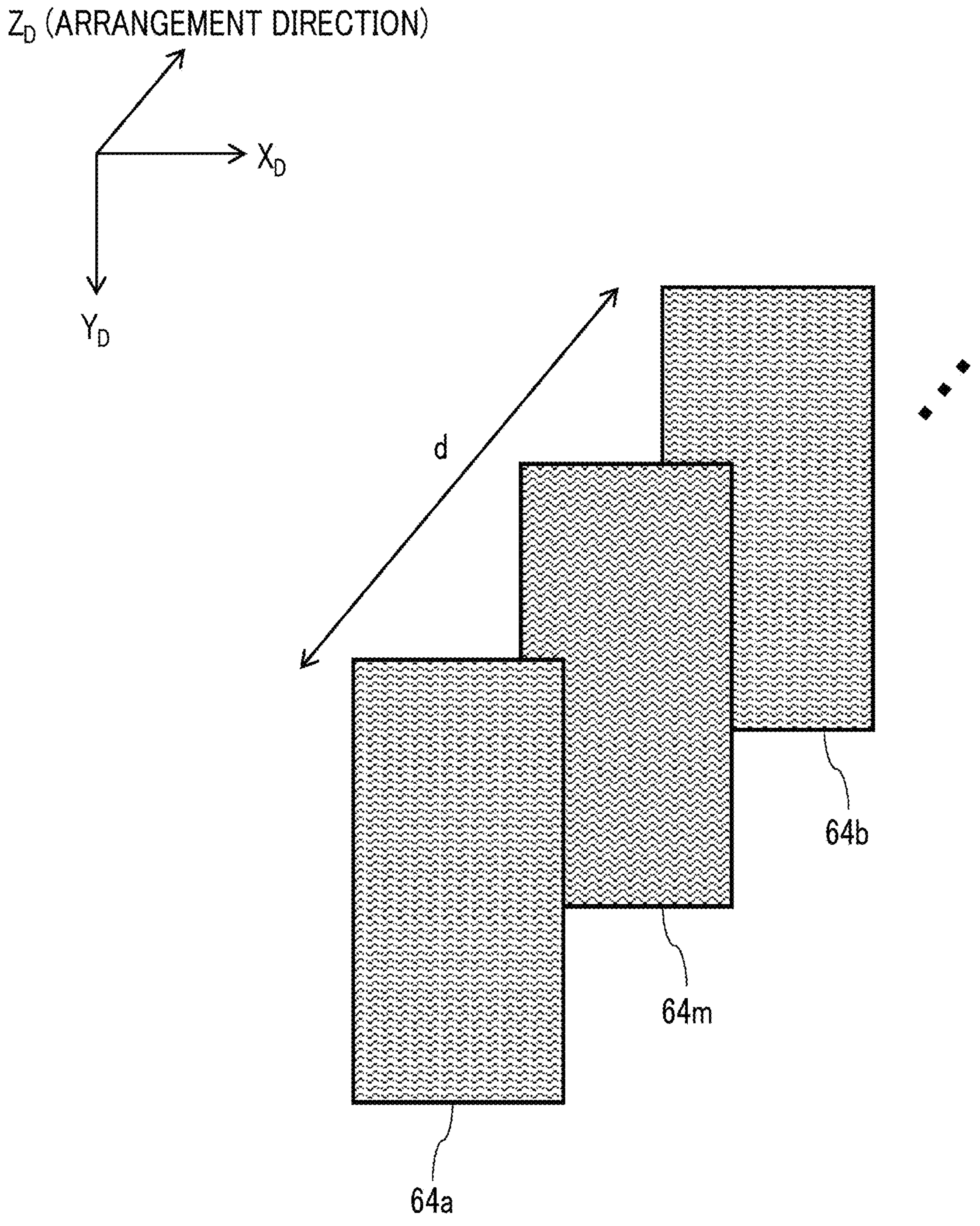
FIG. 11 is a diagram showing intermediate frame data.

FIG. 11 is a diagram showing intermediate frame data 64$m$. In a case where the ultrasound probe 14 is swept to form a plurality of pieces of frame data, and the operator quickly moves the ultrasound probe 14 in the sweep direction, the first sweep position 14$a$ and the second sweep position 14$b$ (see FIG. 6) may become separated. That is, a distance in the sweep direction between the scanning plane SPa and the scanning plane SPb increases. In such a case, in a case where the position of each piece of the frame data 64 in the arrangement direction is determined based on the sweep position of the ultrasound probe 14 included in the position and posture information associated with each piece of the frame data 64, a distance d in the arrangement direction between the first frame data 64$a$ corresponding to the scanning plane SPa and the second frame data 64$b$ corresponding to the scanning plane SPb in the data space becomes large. In a case where the ultrasound volume data 60 is formed in this state, a missing portion of data elements exists between the first frame data 64$a$ and the second frame data 64$b$.

Therefore, the volume data forming unit 50 may generate, based on both pieces of the frame data 64 (in the example of FIG. 11, the first frame data 64$a$ and the second frame data 64$b$) adjacent to each other in the frame data sequence 62, the intermediate frame data 64$m$ disposed between both pieces of the frame data 64. Then, the volume data forming unit 50 may form the ultrasound volume data 60 by using the intermediate frame data 64$m$ as well. The volume data forming unit 50 may form the intermediate frame data 64$m$ in a case where a distance in the sweep direction between the first sweep position 14$a$ and the second sweep position 14$b$ is equal to or greater than a threshold distance.

A known technology can be used as a method of generating the intermediate frame data 64$m$ based on the first frame data 64$a$ and the second frame data 64$b$. For example, the intermediate frame data 64$m$ can be generated by applying a spatio-temporal filter to the first frame data 64$a$ and the second frame data 64$b$. As the filter type, a smoothing filter, an anisotropic filter, an adaptive filter, or a combination thereof can be used. Alternatively, the intermediate frame data 64$m$ may be generated by detecting local variations of the second frame data 64$b$ relative to the first frame data 64$a$ and applying nonlinear correction accordingly.

In a case where the intermediate frame data 64$m$ is generated, the volume data forming unit 50 forms the ultrasound volume data 60 after disposing the intermediate frame data 64$m$ between the first frame data 64$a$ and the second frame data 64$b$ in the arrangement direction. In this case, the intermediate frame data 64$m$ may be disposed at a position midway between the first frame data 64$a$ and the second frame data 64$b$ in the arrangement direction.

Figure 12:
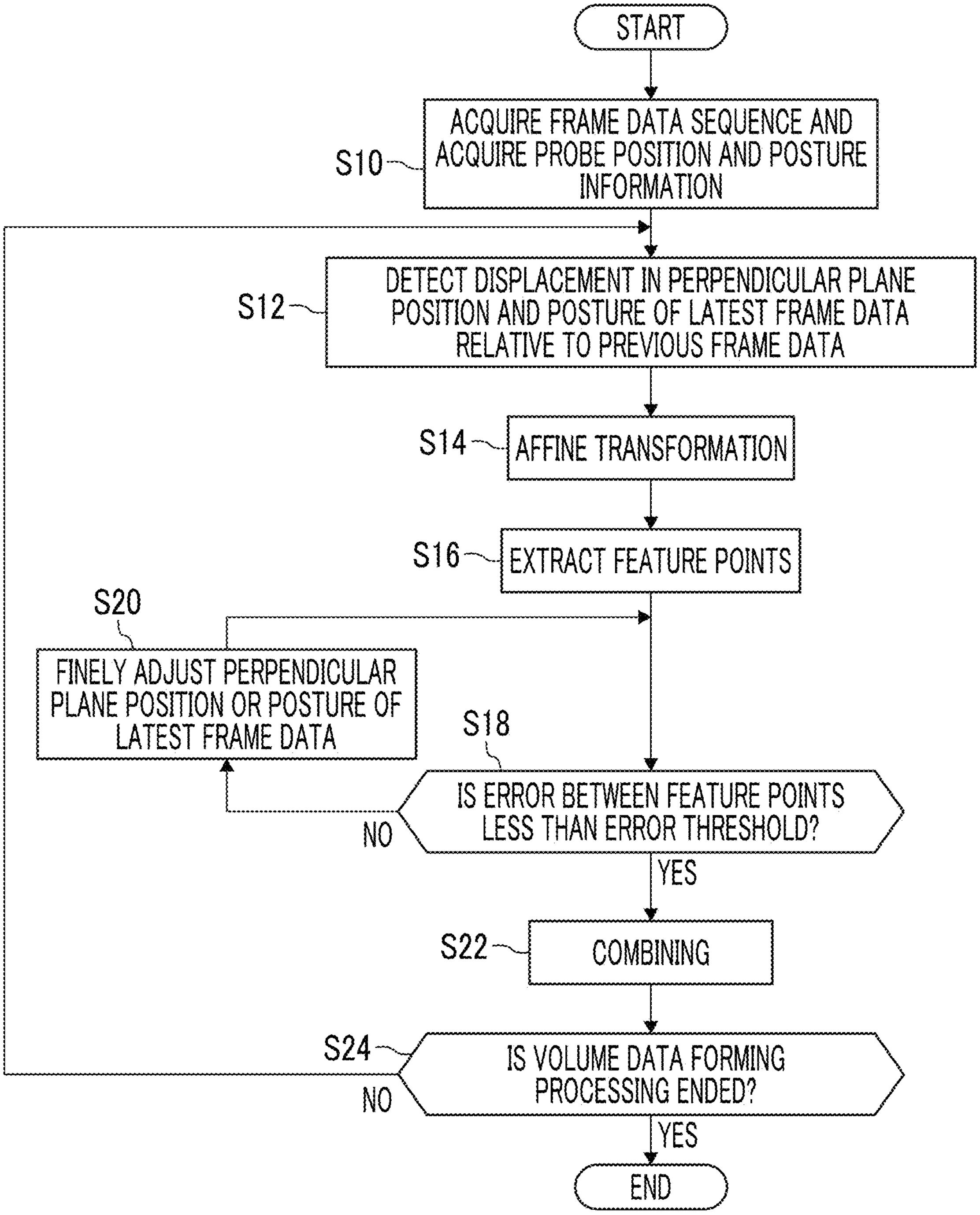
FIG. 12 is a flowchart showing a flow of processing of the ultrasound diagnostic apparatus according to the present embodiment.

An outline of the configuration of the ultrasound volume data forming system 10 according to the present embodiment is as described above. Hereinafter, a flow of the processing of the ultrasound diagnostic apparatus 16 will be described with reference to a flowchart shown in FIG. 12.

In step S10, the frame data sequence 62 including the plurality of pieces of frame data 64 corresponding to each scanning plane SP is acquired while the operator moves the ultrasound probe 14 in the sweep direction. The probe position and posture information acquisition unit 48 acquires the position and posture information indicating the position and the posture of the ultrasound probe 14 when each piece of the frame data 64 for forming the ultrasound volume data 60 is acquired. The probe position and posture information acquisition unit 48 stores each piece of the frame data 64 in the memory 44 in association with the position and posture information indicating the position and the posture of the ultrasound probe 14 when the corresponding frame data 64 is acquired.

In step S12, the volume data forming unit 50 detects, relative to the previous frame data (for example, the first frame data 64*a*), which is the latest frame data 64 combined among the pieces of the frame data 64 that have already been subjected to the combining (in a case where there is no frame data 64 that has been subjected to the combining, the frame data 64 at the head of the frame data sequence 62), a displacement in perpendicular plane position and posture of the latest frame data (for example, the second frame data 64*b*), which is the frame data 64 that is adjacent to the previous frame data in the frame data sequence 62 and that is acquired subsequent to the previous frame data. The detection of the displacement is performed based on the position and posture information associated with the previous frame data and on the position and posture information associated with the latest frame data.

In step S14, the volume data forming unit 50 performs an affine transformation on the latest frame data based on the displacement detected in step S12 such that a relationship of perpendicular plane position and posture between the previous frame data and the latest frame data is the same as a relationship between position and posture information associated with the previous frame data and position and posture information associated with the latest frame data. In other words, at least one of the perpendicular plane position or the posture of the latest frame data is changed.

In step S16, the volume data forming unit 50 extracts feature points from each of the previous frame data and the latest frame data.

In step S18, the volume data forming unit 50 determines whether an error (distance in the $X_DY_D$ plane) between coordinates (see FIG. 9) of the feature point in the $X_DY_D$ plane detected from the previous frame data in the $X_DY_D$ plane and coordinates of the feature point detected from the latest frame data corresponding to the feature point is less than a predetermined error threshold. In a case where the error is equal to or greater than the error threshold, the processing proceeds to step S20.

In step S20, the volume data forming unit 50 finely adjusts the perpendicular plane position or the posture of the latest frame data so as to reduce the error detected in step S18. After the fine adjustment, the volume data forming unit 50 determines again whether the error is less than the error threshold. The volume data forming unit 50 repeats the fine adjustment of the latest frame data until the error becomes less than the error threshold. In a case where it is determined that the error is less than the error threshold, the processing proceeds to step S22.

In step S22, the volume data forming unit 50 combines (stacks) the previous frame data and the latest frame data.

In step S24, the volume data forming unit 50 determines whether the processing of forming the ultrasound volume data 60 has ended, in other words, whether the combining of all the pieces of frame data 64 for forming the ultrasound volume data 60 has ended. In a case where the processing of forming the ultrasound volume data 60 has not ended, the processing returns to step S12, and in step S12 again, the previous frame data and the latest frame data are changed, and the processing of steps S12 to S24 is repeated. In step S24, in a case where it is determined that the processing of forming the ultrasound volume data 60 has ended, the processing ends.

Although the ultrasound volume data forming apparatus according to the present disclosure has been described above, the ultrasound volume data forming apparatus according to the present disclosure is not limited to the above-described embodiment, and various changes can be made without departing from the gist thereof.

For example, in each of the above-described embodiments, the ultrasound volume data forming apparatus is the ultrasound diagnostic apparatus 16, and each of the functions of the frame data sequence acquisition unit and the volume data forming unit 50 is included in the ultrasound diagnostic apparatus 16. However, each of these functions does not necessarily have to be exhibited by the ultrasound diagnostic apparatus 16. For example, these functions may be exhibited by a server computer or the like that is communicatively connected to the ultrasound diagnostic apparatus 16. In that case, a processor of the server computer or the like as the ultrasound volume data forming apparatus acquires the frame data sequence 62 in which the position and posture information of the ultrasound probe 14 is associated with each piece of the frame data 64 (exhibits the function as the frame data sequence acquisition unit), and forms the ultrasound volume data 60 based on the frame data sequence 62 (exhibits the function as the volume data forming unit 50). In addition, all of the above-described functions may not be exhibited by one device, and the above-described functions may be exhibited by cooperation of a plurality of devices.

What is claimed is:

1. An ultrasound volume data forming apparatus comprising a processor configured to:

acquire a frame data sequence acquired by sweeping an ultrasound probe that scans an ultrasound beam on a subject, in a direction perpendicular to a scanning plane of the ultrasound beam, the frame data sequence including each piece of frame data having a data element sequence, two-dimensionally arranged in accordance with the scanning plane, indicating a signal intensity of a reflected wave from the subject, in which position and posture information indicating a perpendicular plane position, which is a position of the ultrasound probe when a piece of the frame data in a plane perpendicular to a sweep direction is acquired, and a posture of the ultrasound probe when the piece of the frame data is acquired is associated with each piece of the frame data included in the frame data sequence; and form ultrasound volume data by arranging the frame data sequence in an arrangement direction that is a direction perpendicular to a two-dimensional array direction of the data element sequence in a data space, wherein the ultrasound volume data is formed by changing at least one of a perpendicular plane position, which is a position in a plane perpendicular to the arrangement direction, or a posture of each piece of the frame data included in the frame data sequence in accordance with the position and posture information associated with the piece of frame data without changing the position and the posture of the ultrasound probe, and then arranging the pieces of the frame data in the arrangement direction.

2. The ultrasound volume data forming apparatus according to claim 1, wherein the processor is configured to extract a first feature point in one piece of the frame data among adjacent pieces of the frame data in the frame data sequence and a second feature point corresponding to the first feature point in the other piece of the frame data, and change at least one of the perpendicular plane position or the posture of each piece of the frame data such that the first feature point and the second feature point are arranged in the arrangement direction.

3. The ultrasound volume data forming apparatus according to claim 1, wherein the processor is configured to form the ultrasound volume data by excluding frame data in which at least one of the perpendicular plane position or the posture has an outlier compared to a plurality of the other pieces of the frame data, based on the position and posture information associated with each piece of the frame data.

4. The ultrasound volume data forming apparatus according to claim 1, wherein the processor is configured to generate, based on both pieces of the frame data adjacent to each other in the frame data sequence, intermediate frame data to be disposed between both pieces of the frame data, and form the ultrasound volume data by using the intermediate frame data.

5. The ultrasound volume data forming apparatus according to claim 1, wherein the position and posture information indicates a perpendicular plane position and a posture of the ultrasound probe relative to a body surface of the subject, based on a captured image acquired by imaging a probe detection marker attached to the ultrasound probe and on a body surface detection marker attached to the body surface of the subject, via a camera.

6. A non-transitory computer-readable storage medium storing an ultrasound volume data forming program causing a computer to:

acquire a frame data sequence acquired by sweeping an ultrasound probe that scans an ultrasound beam on a subject, in a direction perpendicular to a scanning plane of the ultrasound beam, the frame data sequence including each piece of frame data having a data element sequence, two-dimensionally arranged in accordance with the scanning plane, indicating a signal intensity of a reflected wave from the subject, in which position and posture information indicating a perpendicular plane position, which is a position of the ultrasound probe when a piece of the frame data in a plane perpendicular to a sweep direction is acquired, and a posture of the ultrasound probe when the piece of the frame data is acquired is associated with each piece of the frame data included in the frame data sequence; and form ultrasound volume data by arranging the frame data sequence in an arrangement direction that is a direction perpendicular to a two-dimensional array direction of the data element sequence in a data space, wherein the ultrasound volume data is formed by changing at least one of a perpendicular plane position, which is a position in a plane perpendicular to the arrangement direction, or a posture of each piece of the frame data included in the frame data sequence in accordance with the position and posture information associated with the piece of frame data without changing the position and the posture of the ultrasound probe, and then arranging the pieces of the frame data in the arrangement direction.

* * * * *